(12) United States Patent
Nagasawa et al.

(10) Patent No.: US 9,005,898 B2
(45) Date of Patent: Apr. 14, 2015

(54) METHOD FOR CONTROLLING HAIR GROWTH, METHOD FOR SELECTING OR EVALUATING HAIR GROWTH CONTROL AGENT, AND HAIR GROWTH SUPPRESSION AGENT

(75) Inventors: Azumi Nagasawa, Utsunomiya (JP); Susumu Ichinose, Utsunomiya (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 13/821,380

(22) PCT Filed: Sep. 8, 2011

(86) PCT No.: PCT/JP2011/070481
§ 371 (c)(1),
(2), (4) Date: Mar. 7, 2013

(87) PCT Pub. No.: WO2012/033162
PCT Pub. Date: Mar. 15, 2012

(65) Prior Publication Data
US 2013/0216632 A1    Aug. 22, 2013

(30) Foreign Application Priority Data

Sep. 9, 2010 (JP) ................................. 2010-201837
Sep. 9, 2010 (JP) ................................. 2010-201838

(51) Int. Cl.
| | |
|---|---|
| C12Q 1/68 | (2006.01) |
| A61K 36/24 | (2006.01) |
| A61K 8/97 | (2006.01) |
| A61K 36/27 | (2006.01) |
| A61Q 7/02 | (2006.01) |
| G01N 33/68 | (2006.01) |
| A61K 9/00 | (2006.01) |

(52) U.S. Cl.
CPC . *A61K 36/24* (2013.01); *A61K 8/97* (2013.01); *A61K 36/27* (2013.01); *A61Q 7/02* (2013.01); *C12Q 1/6876* (2013.01); *G01N 33/68* (2013.01); *A61K 9/0014* (2013.01)

(58) Field of Classification Search
None
See application file for complete search history.

(56) References Cited

U.S. PATENT DOCUMENTS

| | | |
|---|---|---|
| 2003/0199584 A1 | 10/2003 | Ahluwalia et al. |
| 2005/0249685 A1 | 11/2005 | Botchkareva et al. |
| 2008/0102143 A1 | 5/2008 | Freis et al. |
| 2009/0104295 A1 | 4/2009 | Kohno |
| 2009/0182031 A1 | 7/2009 | Botchkareva et al. |
| 2009/0186024 A1 | 7/2009 | Nevins et al. |
| 2011/0059917 A1 | 3/2011 | Jimenez et al. |
| 2011/0130456 A1 | 6/2011 | Suzuki et al. |

FOREIGN PATENT DOCUMENTS

| | | |
|---|---|---|
| CN | 1562259 A | 1/2005 |
| CN | 1946372 A | 4/2007 |
| CN | 102655869 A | 9/2012 |
| JP | 11-049647 A | 2/1999 |
| JP | 2002-062289 A | 2/2002 |
| JP | 2003-221313 A | 8/2003 |
| JP | 2003-221315 A | 8/2003 |
| JP | 2005-206536 A | 8/2005 |
| JP | 2006-008657 A | 1/2006 |
| JP | 2007-517824 A | 7/2007 |
| JP | 2007-534700 A | 11/2007 |
| JP | 4189024 B | 9/2008 |
| JP | 2008-255078 A | 10/2008 |
| JP | 2012-153660 A | 8/2012 |
| JP | 2012-153661 A | 8/2012 |
| JP | 2013-501790 A | 1/2013 |
| WO | WO 03/086331 A2 | 10/2003 |
| WO | WO 2005/105023 A1 | 11/2005 |
| WO | WO 2006/124836 A1 | 11/2006 |
| WO | WO 2007/020755 A1 | 2/2007 |
| WO | WO 2007/140390 A2 | 12/2007 |
| WO | WO 2010/016606 A2 | 2/2010 |
| WO | WO 2011/019617 A2 | 2/2011 |

OTHER PUBLICATIONS

Zhang et al., "Studies on the Constituents of Asclepiadaceae Plants. LXI. The Structure of Cynatratoside-F from the Chinese Drug "Pai-Wei," Dried Root of *Cynanchum atratum* Bunge" 33(10) Chemical and Pharmaceutical Bulletin 41-88-4192 (1985).*

Parsons et al., "The dnaK/dnaJ operon of *Haemophilus ducreyi* contains a unique combination of regulatory elements" 233 Gene 109-119 (1999).*

Hata et al., "Characterization of HSE sequences in human Hsp40 gene: structural and promoter analysis" 1397 Biochimica et Biophysica Acta 43-55 (1998).*

(Continued)

*Primary Examiner* — Celine Qian
*Assistant Examiner* — Nancy J Leith
(74) *Attorney, Agent, or Firm* — Sterne, Kessler, Goldstein & Fox P.L.L.C.

(57) ABSTRACT

The present invention provides a method for controlling hair growth, a method for selecting or evaluating a hair growth control agent, and a hair growth suppression agent. The present invention provides a method for selecting or evaluating a hair growth control agent, including the steps of administering a test substance to a cell capable of expressing DnaJC6; measuring the expression of DnaJC6 in the cell; and evaluating the controlling effect of the test substance on hair growth based on the expression. The present invention also provides a hair growth suppression agent containing funabarasou (*Cynanchum atratum*) or its extract as the active ingredient.

19 Claims, 4 Drawing Sheets

(56) References Cited

OTHER PUBLICATIONS

Ohtsuka et al., "Molecular chaperone function of mammalian Hsp70 and Hsp40—a review" 16(3) International Journal of Hyperthermia 231-245 (2000).*

International Search Report (ISR) for PCT/JP2011/070481; I.A. fd: Sep. 8, 2011, mailed Dec. 20, 2011 from the Japanese Patent Office, Tokyo, Japan.

International Preliminary Report on Patentability (IPRP), Chapter I of the Patent Cooperation Treaty, including the Written Opinion for PCT/JP2011/070481; I.A. fd: Sep. 8, 2011, issued Apr. 9, 2013, from the International Bureau of WIPO, Geneva, Switzerland.

Jindo, T et al., "Organ culture of mouse vibrissal hair follicles in serum-free medium," J. Dermatol., 20(12):756-762 (Dec. 1993), Japanese Dermatological Assoication, Tokyo, Japan.

Uzuka, M. et al., "Adult mouse vibrissa follicles in organ culture: effects of growth factors and drugs on hair growth," Jpn. J. Dermatol. 104(8): 979-987 (1994), Japanese Dermatological Association, Tokyo, Japan.

Philpott, MP et al., "Human hair growth in vitro," J. Cell Sci. 97: 463-471 (Nov. 1990), Company of Biologists, Cambridge, England.

Wikipedia entry for "Heat shock protein," printed from en.wikipedia.org/wiki/Heat_shock_protein, on Nov. 13, 2014.

Yokota, S. et al., "Benzylidene Lactam Compound, KNK437, a Novel Inhibitor of Acquisition of Thermotolerance and Heat Shock Protein Induction in Human Colon Carcinoma Cells," Cancer Res., Jun. 2000; 60: 2942-2948, Amer. Assoc Cancer Res., Baltimore, MD.

Calderwood, SK et al., "The shock of aging: molecular chaperones and the heat shock response in longevity and aging—a mini-review," Gerontology, Jan. 2009; 55(5): 550-558, Karger, New York.

Homma, S et al., "Demyelination, Astrogliosis, and Accumulation of Ubiquitinated Proteins, Hallmarks of CNS Disease in hsf1-Deficient Mice," J. Neurosci., Jul. 2007; 27: 7974-7986, Society for Neuroscience, Washington, DC.

* cited by examiner

SEQUENCE LISTING

<160> NUMBER OF SEQ ID NOS: 5

<210> SEQ ID NO 1
<211> LENGTH: 979
<212> TYPE: DNA
<213> ORGANISM: Homo sapiens
<220> FEATURE:
<221> NAME/KEY: promotor
<222> LOCATION: (1)..(979)
<223> OTHER INFORMATION: DnaJC6

<400> SEQUENCE: 1

```
acagcattta ttgccattta ttatatgtct atattacctg tctgaatcct cccaccagag    60
tgcaataacc aagaaggcag ggacctgaaa ccctaagagg tggaatagtg cctggcacaa   120
ataaccacgt gttgaataaa tgattgaatt aatgaatgaa tctgagctgt ggaatgattc   180
aaagtaagtt tgaattgaat gactgaaaga tttacttgaa tcctccttgc tccccaacag   240
aggggtgtta tggtttggca tcctcataca tattcctagt ctgccactca atggcttaca   300
accagtcact aaagcctcct tgagtatcaa cttaggcctg ggtgaaatgg gttcaataac   360
ctgtgtccat gcagcagaca cagcccatta tattgccctg tatgcctctg tactgtaaca   420
gcctgtgagc agcgtgagga ccgagggctg gtcctgtgca ctgttgtatc cccagtactt   480
agcatacagc ctggtccaca gagaggtaaa ataaatgttg aatgaatgaa tgaaagtaca   540
gggctctgaa tcctcctcca aagctgactt accatctgaa aataaacctg gtgcatggca   600
cagacattcc cctttcaatt cagagatgag gaggcgctaa acagttggtt ccctatcctg   660
agggaaggaa aggcaagcct cggctccaga tccggttcca tgccatgttt tggaatttgt   720
gtttacgtct gccttcatcc ccatcctttc cgctccagca taagcaaaat tataaccccg   780
cacaccgact tgcatgcaat tatcatagcc cgagtgctcc tccgttgaga gacttcgccc   840
ccgagaccgc tgactgtgaa tgacaaatca aaagtcaggg ttgcagaatc agccggactt   900
tcctgctcat ttgcagcaga gggaggaagc agagaatgaa agattctgaa aataaaggta   960
aggggcggac tgcagaaag                                                979
```

<210> SEQ ID NO 2
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 2

```
caggaaagtg agcaatcaga tga                                            23
```

<210> SEQ ID NO 3
<211> LENGTH: 20

```
<212> TYPE: DNA
<213> ORGANISM: Artificial sequence
<220> FEATURE:
<223> OTHER INFORMATION: Oligonucleotide as PCR primer

<400> SEQUENCE: 3
ggcttgtcac cattggcatt                                               20

<210> SEQ ID NO 4
<211> LENGTH: 22
<212> TYPE: DNA
<213> ORGANISM: Artificial sequence
<220> FEATURE:
<223> OTHER INFORMATION: Oligonucleotide as PCR primer

<400> SEQUENCE: 4
tcctgagtga tgtgcagctg at                                            22

<210> SEQ ID NO 5
<211> LENGTH: 23
<212> TYPE: DNA
<213> ORGANISM: Artificial sequence
<220> FEATURE:
<223> OTHER INFORMATION: Oligonucleotide as PCR primer

<400> SEQUENCE: 5
agcacttcag ggttgtagat gct                                           23
```

METHOD FOR CONTROLLING HAIR GROWTH, METHOD FOR SELECTING OR EVALUATING HAIR GROWTH CONTROL AGENT, AND HAIR GROWTH SUPPRESSION AGENT

REFERENCE TO SEQUENCE LISTING SUBMITTED ELECTRONICALLY

The content of the electronically submitted substitute sequence listing, file name 25370830002_SequenceListing_ascii, size 2,693 bytes; and date of creation Apr. 24, 2013, filed herewith, is incorporated herein by reference in its entirety.

FIELD OF THE INVENTION

The present invention relates to a method for controlling hair growth, a method for selecting or accused evaluating a hair growth control agent, and a hair growth suppression agent.

BACKGROUND OF THE INVENTION

From the viewpoint of biology, head hair and body hair are tissues that protect important organs and body parts, such as the head, chest, and limbs. However, in recent years, there has been an increasing tendency that little body hair on particular body parts (e.g., limbs) is considered favorable from the viewpoint of aesthetic appearance.

Examples of a body hair removal method include a mechanical removal method using a shaver, a hair remover, or the like, and a chemical removal method using an epilation or depilation agent. However, such body hair removal methods may involve physical or chemical stimulation of the skin, and further, are not yet satisfactory in terms of hair growth suppressing effect. Thus, the aforementioned methods require a retreatment for body hair removal after the elapse of a certain period of time. Thus, demand has arisen for reducing the frequency of body hair removal treatments.

Conventionally, in the selection or evaluation of a hair growth agent or a hair growth suppression agent, a candidate substance was applied to the skin of a living body (Patent Documents 1 to 3) or administered to the organ culture of hair follicles of human, mouse, rat, or pig in vitro, subsequently the degree of the extension of hair or the growth of the hair follicle was measured, and the hair-growing or hair-suppressing action of the candidate substance was evaluated based on the results of the measurement (Patent Documents 4 to 7, Non Patent Documents 1 to 3). Considering the efficiency and the accuracy of the evaluation, an in vitro assay is more preferable. However, there are problems with in vitro organ culture of hair follicles that acquisition of the hair follicle to be used as a sample may be difficult, culture takes time and labor, and evaluation is time-consuming as it takes several days until the extension of hair or the growth of the hair follicle is observed, and so on. The development of an in vitro screening system for more efficient selection or evaluation of a hair growth agent or a hair growth suppression agent is demanded.

Patent Document 7 describes that such heat shock proteins as HSP-27, HSP-70, and HSP-90 are present in the human hair follicle, that administration of an anti-HSP-27 antibody to the hair follicle led to an observation of a significant reduction in the development of hair fiber, and that the growth of the human hair follicle was reduced by administration of geldanamycin, which is an HSP-90-specific inhibitor, or KNK437, which is an HSP synthesis-inhibitor, in a dose-dependent manner. However, given that there are so many kinds of heat shock proteins and their functions are also diverse, the molecular mechanisms involved in hair growth of the aforementioned heat shock proteins remain unknown, and further, it has been impossible to predict whether other heat shock proteins could be involved in hair growth.

Funabarasou (*Cynanchum atratum*) is a perennial plant belonging to the genus *Cynanchum* in the family Asclepiadaceae, and its root is used in a Kampo prescription such as byakubito. Funabarasou (*Cynanchum atratum*) is known to have a medicinal effect such as alleviation of fever and cooling of blood, antipyresis, and a diuretic effect. Further, cynanchol, which has the action of cardiac glycosides, is known as its medicinal ingredient.

Patent Document 8 discloses a skin external preparation for hair growth containing an extract of a crude drug, including byakubi, having an activating action of body fluids (shinekisayou) and the active ingredient of the extract as well as an extract of a crude drug having an angiogenesis activation action and the active ingredient of the extract. Patent Document 9 describes the use of a composition containing the extract of a plant belonging to the family Asclepiadaceae for the cosmetic treatment of human skin including inhibition, suppression, or retardation of the growth of the body hair. However, it has not been revealed how funabarasou (*Cynanchum atratum*) affects hair growth by itself.

CITATION LIST

Patent Document

Patent Document 1: WO03/086331
Patent Document 2: JP-A-2005-206536
Patent Document 3: JP-A-2006-008657
Patent Document 4: WO2010/016606
Patent Document 5: JP-A-11-49647
Patent Document 6: JP-A-2002-62289
Patent Document 7: JP-B-4189024
Patent Document 8: JP-A-2003-221313
Patent Document 9: JP-A-2007-517824

Non Patent Document

Non Patent Document 1: Jindo et al., The Journal of Dermatology, Vol., 20: 756 to 762, 1993.
Non Patent Document 2: Makoto Uzuka and Chika Hanzawa, The Japanese Journal of Dermatology, 104 (8); 979 to 987, 1994.
Non Patent Document 3: Philpott et al., Journal of Cell Science, 97: 463 to 471, 1990.

SUMMARY OF THE INVENTION

That is, according to one aspect, the present invention provides a method for controlling hair growth, comprising a step of controlling the activation level of DnaJC6 in a hair tissue.

According to another aspect, the present invention provides a method for selecting or evaluating a hair growth control agent, comprising the following steps (A) to (C):

(A) measuring the expression level of DnaJC6 in a cell capable of expressing DnaJC6 in the presence and absence of a test substance;

(B) comparing the expression level of DnaJC6 in the cell in the presence of the test substance and the expression level of DnaJC6 in the cell in the absence of the test substance; and (C) selecting, when there is a significant difference in the expression level of DnaJC6 between the presence and absence of the test substance, the test substance as a hair growth control agent.

Yet another aspect of the present invention is funabarasou (*Cynanchum atratum*) or its extract for use in suppression of hair growth, or use of funabarasou (*Cynanchum atratum*) or its extract in the production of a medicine or cosmetics for suppression of hair growth.

Further, according to another aspect, the present invention provides a method for suppressing hair growth, comprising applying funabarasou (*Cynanchum atratum*) or its extract to a skin tissue where suppression of hair growth is desired.

Also, according to another aspect, the present invention provides a hair growth suppression agent comprising funabarasou (*Cynanchum atratum*) or its extract as the active ingredient.

DETAILED DESCRIPTION OF THE INVENTION

Figure 1:
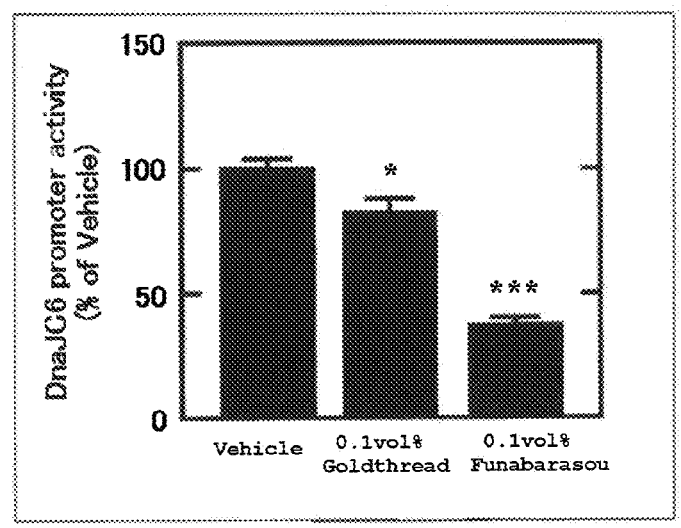
FIG. 1 shows the effect of an extract of goldthread (*Coptis japonica*) and an extract of funabarasou (*Cynanchum atratum*) on the promoter activity of human DnaJC6. In the figure, n=3, mean±SD, *: P<0.05, ***: P<0.001 (non-paired t-test, vs Vehicle).

In the present specification, the term "non-therapeutic" refers to a concept which does not include medical practice, i.e., the act of treatment of the human body by therapy.

In the present specification, the term "controlling hair growth" refers to a promoting or suppressing action on the extension of hair or hair follicles or an increasing or decreasing action on the diameter of the hair. That is, the term "controlling hair growth" in the present specification refers to the concept which includes promotion and suppression of hair growth.

In the present specification, the term "DnaJC6" refers to a protein registered under MIM ID *608375 in the NCBI database (OMIM) [www.ncbi.nlm.nih.gov/sites/entrez?db=omim]. DnaJC6 is a protein which is classified into heat shock protein. Numerous families exist for heat shock proteins, and for example, a heat shock protein is roughly classified into the following families; HSP110, HSP90, HSP70, HSP60, HSP40, HSP27, and HSP10. Among them, DnaJC6 is a molecular chaperone belonging to the DNAJ/HSP40 family.

In the present specification, the terms "DnaJC6 gene", "DnaJC6 mRNA", and "DnaJC6 promoter" refer to a gene encoding DnaJC6, its mRNA, and a promoter controlling the gene encoding DnaJC6, respectively.

The present invention relates to a method for controlling hair growth by regulating gene expression, a method for selecting or evaluating a hair growth control agent using gene expression as an index, and a hair growth suppression agent.

The present inventors found that regulating the expression of DnaJC6 enables control of hair growth, the use of DnaJC6 expression as an index enables efficient selection or evaluation of a substance which controls hair growth, and as a result of searching for a substance which suppresses hair growth, that funabarasou (*Cynanchum atratum*) or its extract has a suppressing effect on hair growth.

According to the present invention, hair growth can be controlled in the desired location in the body of an animal. Also, according to the present invention, a hair growth control agent can be selected or evaluated simply, rapidly, and efficiently in vitro. Also, according to the present invention, suppression of hair growth can be realized using a plant-derived, highly effective raw material which is safe for the living body.

According to one aspect, the present invention provides a method for controlling hair growth, including a step of regulating the activation level of DnaJC6 in a hair follicle tissue.

Examples of the aforementioned tissue include a tissue of the living body of an animal and a tissue derived from the living body of an animal. Examples of the animal include preferably a human or a non-human mammal, more preferably a human. Further, examples of the animal preferably include an animal in need of controlling hair growth such as an animal in which hair generation or hair growth is desired or not desired, an animal in which hair depilation or hair epilation is desired, and an animal in which hair epilation is not desired. Examples of the tissue derived from the living body include a tissue collected from an animal and a culture product of such a tissue.

The aforementioned regulation of the activation level can be carried out by regulating the amount of a DnaJC6 protein present, activation of the DnaJC6 protein, the DnaJC6 protein expression, the expression of a gene encoding the DnaJC6 protein or its mRNA, or the activation of a promoter of the gene encoding the DnaJC6 protein in the aforementioned tissues. They can be regulated alone or in combination.

According to one embodiment, the aforementioned step of controlling can be a step of suppressing hair growth by reducing the activation level of DnaJC6.

Examples of the means for reducing the activation level of DnaJC6 include deactivation of the DnaJC6 protein using a DnaJC6 protein-specific antibody, suppression of transcription of the DnaJC6 gene into mRNA by inhibiting the promoter activity of the DnaJC6 gene, and suppression of translation of DnaJC6 mRNA into a protein by means of RNAi and the like.

According to a preferred embodiment, the aforementioned activation level is reduced preferably by 20% or more, more preferably by 50% or more in terms of the promoter activity of the DnaJC6 gene. Alternatively, the aforementioned activation level is reduced preferably by 10% or more, more preferably by 20% or more in terms of the expression level of DnaJC6 mRNA. Hair growth in the aforementioned tissues is suppressed by a reduction in the activation level of DnaJC6.

According to another embodiment, the aforementioned step of controlling can be a step of promoting hair growth by increasing the activation level of DnaJC6.

Examples of the means for increasing the activation level of DnaJC6 include introduction of the DnaJC6 gene into cells of the aforementioned tissues, introduction of an expression vector carrying the DnaJC6 gene into cells of the aforementioned tissues, promotion of transcription of the DnaJC6 gene into mRNA by increasing the promoter activity of the DnaJC6 gene, suppression of the degradation of DnaJC6 mRNA, and suppression of the degradation of the DnaJC6 protein.

According to a preferred embodiment, the aforementioned activation level is increased preferably by 20% or more, more preferably by 50% or more in terms of the promoter activity of the DnaJC6 gene. Alternatively, the aforementioned activation level is increased preferably by 10% or more, more preferably by 20% or more in terms of the expression level of DnaJC6 mRNA. Hair growth in the aforementioned tissues is promoted by an increase in the activation level of DnaJC6.

According to another aspect of the present invention, a method for selecting or evaluating a hair growth control agent, including the following steps (A) to (C), is provided:

(A) measuring the expression level of DnaJC6 in a cell capable of expressing DnaJC6 in the presence and absence of a test substance;

(B) comparing the expression level of DnaJC6 in the cell in the presence of the test substance and the expression level of DnaJC6 in the cell in the absence of the test substance; and (C) selecting, when there is a significant difference in the expression level of DnaJC6 between the presence and absence of the test substance, the test substance as a hair growth control agent.

Examples of the aforementioned "cell capable of expressing DnaJC6" include a cell which naturally possesses the DnaJC6 gene and is capable of expressing the gene, and a cell into which the DnaJC6 gene is exogenously introduced in such a way that the gene can be expressed. This cell may be a cell collected from a living body or a cell contained in a tissue or organ collected from the living body, or it may be a cultured cell. Preferably, this cell is derived from a mammal. Examples of the cell which naturally possesses the DnaJC6 gene and is capable of expressing the gene include a cell which is derived from any tissue in a living body, and preferably, it is a cell derived from the skin collected from a mammal, for example, a cell present in a skin section of a mammal, a cell derived from a hair tissue, a cell derived from an epidermal tissue, a cell derived from a dermal tissue (such as a fibroblast), and a cell derived from the brain as well as a cell culture product derived from the aforementioned cells, and a higher order culture product such as an organ culture product. The cell which is exogenously made capable of expressing the DnaJC6 gene can be obtained by introducing an expression vector into which the DnaJC6 gene is incorporated into an arbitrary mammalian cell, thereby transforming the cell. A method for producing an expression vector into which the DnaJC6 gene is incorporated and a method for introducing the expression vector into a mammalian cell are commonly known to those skilled in the art.

The aforementioned test substance is not particularly limited as long as it is a substance which is desired to be used as a hair growth control agent, and examples thereof include an animal, a plant, a marine organism, a microorganism, and the like, and an extract of these organisms; a natural component derived from the above organisms or extracts; a synthetic compound; and a mixture and a composition of the above organisms and substances.

In the aforementioned step (A), the expression level of DnaJC6 in the cell capable of expressing DnaJC6 is measured in the presence and absence of the test substance. For example, the expression level of DnaJC6 is each measured before and after the administration of the test substance to the cell, in the test substance-addition group and in the test substance-non-addition group, or in the test substance-addition group and in the control substance-addition group.

The expression level of DnaJC6 can be measured using the DnaJC6 protein expression, the expression level of a gene encoding the DnaJC6 protein or its mRNA, the activation level of a promoter of the gene encoding the DnaJC6 protein, and the like as an index. These indices can be measured alone or in combination. Measurement can be performed in accordance with a method which is publicly known in the art as a method for measuring the parameter to be used as an index (for example, protein expression, expression of a gene or mRNA, and the activation of a promoter).

Examples of a method for measuring the expression level of a gene encoding a DnaJC6 protein or its mRNA include polymerase chain reaction (PCR) such as RT-PCR and Real-time RT-PCR, Northern blotting, RNase protection assay, and DNA array analysis.

Also, examples of a method for measuring the expression level of a DnaJC6 protein include, but are not limited to, agarose gel electrophoresis, SDS-PAGE, chromatography, immunoassay (such as immunohistochemistry, ELISA, RIA, Western blotting, and immunoprecipitation, all of which use a DnaJC6 protein-specific antibody), colorimetric determination method, fluorescence-optical measurement, mass analysis, electron microscopy, and a combination of the above measurement methods. Among them, Western blotting, ELISA, or RIA using a DnaJC6 protein-specific antibody is preferable.

In the aforementioned step (B), the measurement values obtained by the aforementioned (A) are compared between the case in which the test substance is present and the case in which the test substance is absent. For example, the measurement values are compared before and after the administration of the test substance or between the test substance-addition group and the test substance-non-addition group or the control substance-addition group. For example, the DnaJC6 protein expression level, the expression level of the gene encoding the DnaJC6 protein or its mRNA, the activation level of the promoter of the gene encoding the DnaJC6 protein, and the like measured in (A) are compared before and after the administration of the test substance, between the test substance-addition group and the test substance-non-addition group, or between the test substance-addition group and the control substance-addition group. Preferably, they are compared using statistical measures.

In the aforementioned step (C), based on the results of comparison obtained by the aforementioned (B), the controlling effect of the test substance on hair growth is evaluated. A substance which has affected the expression of DnaJC6 can be selected as a hair growth control agent. For example, when there is a significant difference in the expression level of DnaJC6 in the aforementioned cell between the presence and absence of the test substance, the test substance can be selected as a hair growth control agent.

According to one embodiment, a test substance which reduces the expression level of DnaJC6 is selected as a hair growth suppression agent. As a preferable example, when the expression level of DnaJC6 mRNA is reduced preferably by 10% or more, more preferably by 20% or more in the presence of the test substance in comparison with the case in which the test substance is absent, the substance is selected as a hair growth suppression agent. The reduction in the expression level is preferably statistically significant.

According to another embodiment, a test substance which increases the expression level of DnaJC6 is selected as a hair growth promoting agent. As a preferable example, when the expression level of DnaJC6 mRNA is increased preferably by 10% or more, more preferably by 20% or more in the presence of the test substance in comparison with the case in which the test substance is absent, the substance is selected as a hair growth promoting agent. The increase in the expression level is preferably statistically significant.

When the expression of DnaJC6 is measured using the activation of the DnaJC6 gene promoter as an index, a method including the following steps (a) to (d) is given as a preferred example:

(a) introducing a reporter gene which is regulated by the promoter of the gene encoding DnaJC6 into a cell capable of expressing DnaJC6;

(b) measuring the amount of the expression product of the reporter gene in the cell in the presence and absence of a test substance;

(c) comparing the amount of the expression product of the reporter gene in the cell in the presence of the test substance and the amount of the expression product of the reporter gene in the cell in the absence of the test substance; and (d) selecting, when there is a significant difference in the amount of the expression product of the reporter gene between the presence and absence of the test substance, the test substance as a hair growth control agent.

As the promoter used for the measurement, a human DnaJC6 promoter is preferable. Examples of the human DnaJC6 promoter include a promoter which has the base sequence shown in SEQ ID NO: 1 and a promoter which has a base sequence resulting from substitution, deletion, insertion, or addition of one to several (preferably one to 10, more preferably one to five) bases occurring in the base sequence shown in SEQ ID NO: 1 and which is regulated by a transcription factor which is similar to that for the promoter having the base sequence shown in SEQ ID NO: 1, thereby regulating the downstream gene expression.

In the aforementioned (a), the reporter gene which is regulated by the promoter of the gene encoding DnaJC6 is introduced into the cell capable of expressing DnaJC6. Preferably, the reporter gene is operably linked to downstream of the above promoter. In a preferable embodiment, the aforementioned reporter gene is selected from the group consisting of luciferase, chloramphenicol acetyltransferase, β-galactosidase, β-glucuronidase, and a green fluorescent protein.

Except that the subject of measurement is the amount of the expression product of the reporter gene, the aforementioned (b) to (d) are the same as the aforementioned (A) to (C). That is, in the aforementioned (d), when there is a significant difference in the amount of the expression product of the reporter gene in the aforementioned cell between the presence and absence of the test substance, the test substance can be selected as a hair growth control agent.

According to one embodiment, a test substance which reduces the amount of the expression product of the aforementioned reporter gene can be selected as a hair growth suppression agent, and a test substance which increases the amount of the expression product of the reporter gene can be selected as a hair growth promoting agent. Preferably, when the amount of the expression product of the reporter gene is reduced preferably by 20% or more, more preferably by 50% or more in the presence of the test substance in comparison with the case in which the test substance is absent, the substance can be selected as a hair growth suppression agent. Also, preferably, when the amount of the expression product of the reporter gene is increased preferably by 20% or more, more preferably by 50% or more in the presence of the test substance in comparison with the case in which the test substance is absent, the substance can be selected as a hair growth promoting agent. The reduction in the expression level is preferably statistically significant.

The hair growth control agent thus obtained can be used for hair generation, hair growth, hair depilation, hair epilation, suppression of hair generation, and the like, or it can be an active ingredient of a hair generation agent, a hair growth agent, a hair depilation agent, an epilation agent, a hair generation-suppressing agent, and the like. Further, by administering the hair growth control agent to a subject in need of promotion or suppression of hair growth such as hair generation, hair growth, hair depilation, hair epilation, and suppression of hair generation, hair growth can be promoted or suppressed in the subject, whereby hair generation, hair growth, hair depilation, hair epilation, suppression of hair generation, and the like can be realized. Moreover, the hair growth control agent can be used as a composition, a medicine, a quasi drug, cosmetics, a food, or a drink for hair generation, hair growth, hair depilation, hair epilation, suppression of hair generation, and the like, or for the production of the above substances.

As will be demonstrated in Examples described below, the present inventors found that an extract of funabarasou (*Cynanchum atratum*) has a significant suppressing action on the extension of organ culture of human hair. Accordingly, funabarasou (*Cynanchum atratum*) or its extract is useful as a hair growth suppression agent. Also, funabarasou (*Cynanchum atratum*) or its extract can exert an effect such as suppression of hair generation or hair growth, or hair depilation, hair epilation, or the like via its suppressing action on hair growth. That is, funabarasou (*Cynanchum atratum*) or its extract can be used for suppression of hair growth, suppression of hair generation or hair growth, or for hair depilation, hair epilation, or the like. The aforementioned use can be conducted in a human or a non-human animal, or in a specimen derived from a human or a non-human animal, and the use may be either therapeutic or non-therapeutic.

As described above, according to one aspect, the present invention provides a hair growth suppression agent containing funabarasou (*Cynanchum atratum*) or its extract as the active ingredient. According to one embodiment, the hair growth suppression agent of the present invention is essentially composed of funabarasou (*Cynanchum atratum*) or its extract. This hair growth suppression agent can be used for suppression of hair generation or hair growth, or for hair depilation or hair epiliation.

In the present specification, the term "funabarasou" refers to *Cynanchum atratum*, which is a perennial plant belonging to the genus *Cynanchum* in the family Asclepiadaceae, and the term "extract of funabarasou" refers to an extract obtained from funabarasou (*Cynanchum atratum*). The extract may be an extract of any part of funabarasou (*Cynanchum atratum*), for example the whole plant or root, or a combination thereof, and an extract of root is preferable. The aforementioned part can be subjected directly to an extraction step or subjected to an extraction step after pulverization, cutting, or drying.

As the aforementioned extract, a commercially available product may be used, or a variety of solvent extracts obtained by a routine method or their dilutions, concentrates, dried powders, pastes, or the above substances after treatment with activated carbon may be used. For example, the funabarasou (*Cynanchum atratum*) extract of the present invention can be obtained by extracting funabarasou (*Cynanchum atratum*) at room temperature (for example, 4 to 50° C.) or by heating (room temperature to a boiling point of a solvent), or by extracting it using an extraction apparatus such as a Soxhlet extractor.

As the solvent for extraction, either a polar solvent or a non-polar solvent can be used. Specific examples of the solvent include water; alcohols such as methanol, ethanol, propanol, and butanol; polyhydric alcohols such as propylene glycol and butylene glycol; ketones such as acetone and methyl ethyl ketone; esters such as methyl acetate and ethyl acetate; chain or cyclic ethers such as tetrahydrofuran and diethyl ether, polyethers such as polyethylene glycol; hydrocarbons such as squalane, hexane, cyclohexane, and petroleum ether; aromatic hydrocarbons such as toluene; halogenated hydrocarbons such as dichloromethane, chloroform, and dichloroethane; and, supercritical carbon dioxide; pyridines; organic solvents such as other oils, for example fat and wax; and a mixture of the above substances. Preferable examples include water, alcohols, and aqueous solutions of alcohols, and as the alcohols, ethanol is preferable. More preferable solvents are water and the aqueous solution of ethanol.

The blending ratio (volume ratio) of alcohols and water in the aqueous solution of alcohol is preferably 0.001 to 100:99.999 to 0, more preferably 5 to 95:95 to 5, even more preferably 20 to 80:80 to 20, still more preferably 30 to 70:70 to 30, and yet still more preferably 40 to 60:60 to 40. In the case of the aqueous solution of ethanol, the concentration of ethanol is preferably 40 to 60 vol %. The amount of solvent used is preferably 1 to 100 mL relative to one g of the root of funabarasou (*Cynanchum atratum*) (in terms of dry mass) and the extraction time is preferably one minute to two months, more preferably 10 minutes to four weeks. At this time, the extraction temperature is 0° C. to the boiling point of the solvent, more preferably 10 to 60° C., and even more preferably 15 to 40° C.

As the means for obtaining an extract, specifically, means such as solid-liquid extraction, liquid-liquid extraction, immersion, decoction, leaching, reflux extraction, ultrasonic extraction, microwave extraction, and stirring can be used. As a preferable example of immersion, immersion can be performed at 15 to 40° C. for one hour to four weeks. Also, when the extraction time is to be shortened, solid-liquid extraction with stirring is desirable. One example of preferable conditions of solid-liquid extraction includes stirring at 10 to 100° C. (preferably 20 to 100° C.) at 1000 to 5000 rpm for one to 30 minutes. In order to prevent oxidation of the extract, means of extraction conducted under a so-called non-oxidative atmosphere can be used in combination while removing dissolved oxygen by boiling deaeration or infusion of an inert gas such as a nitrogen gas.

Funabarasou (*Cynanchum atratum*) or its extract can be used as a composition, medicine, quasi drug, cosmetic, food, or drink for suppression of hair growth or suppression of hair generation or hair growth, or for hair depilation or hair epilation, or its raw ingredient, or as a feed or its raw ingredient. Alternatively, funabarasou (*Cynanchum atratum*) or its extract can be used for the production of the above substances. The aforementioned composition, medicine, quasi drug, cosmetics, food, or drink, or its raw ingredient, or the aforementioned feed or its raw ingredient can be produced or used for a human or a non-human mammal.

Alternatively, funabarasou (*Cynanchum atratum*) or its extract can be blended, as a raw material, into a composition, medicine, quasi drug, cosmetics, food, drink, or feed for suppression of hair growth or suppression of hair generation or hair growth, or for hair depilation or hair epilation, or into a raw ingredient of the food, drink, or feed.

The aforementioned medicine or quasi drug contains funabarasou (*Cynanchum atratum*) or its extract as the active ingredient. This medicine or quasi drug can be administered in any dosage form. As to the dosage form, the above medicine or quasi drug can be administered either orally or parenterally in the form of, for example, an external preparation. Examples of the oral dosage form include a solid dosage form such as a tablet, a coated tablet, a granule, a powder, and a capsule as well as a liquid dosage form such as an elixir, a syrup, and a suspension. Examples of the parenteral dosage form include an injection, an infusion solution, a transdermal dosage form, a transmucosal dosage form, a nasal dosage form, an enteral dosage form, an inhalation dosage form, a suppository, a bolus dosage form, and a patch.

The aforementioned medicine and quasi drug can contain funabarasou (*Cynanchum atratum*) or its extract alone or in combination with a pharmaceutically acceptable carrier. Examples of the carrier include an excipient, a coating agent, a binder, an expander, a disintegrant, a surfactant, a lubricant, a diluent, a dispersant, a buffer, an osmotic pressure adjuster, a pH adjuster, an emulsifier, a preservative, a stabilizer, an antioxidant, a colorant, an ultraviolet ray absorber, a humectant, a thickener, an activity enhancer, an anti-inflammatory agent, a germicide, a fragrance, a flavor corrective, and an odor corrective. Also, as long as the suppressing action of funabarasou (*Cynanchum atratum*) or its extract on hair growth is not lost, the above medicines and quasi drugs can contain other active ingredients and pharmacological ingredients.

The aforementioned medicine or quasi drug can be produced from funabarasou (*Cynanchum atratum*) or its extract, or by combining the aforementioned carriers and/or other active ingredients and pharmacological ingredients as needed, according to a routine method. The content of funabarasou (*Cynanchum atratum*) or its extract in the medicine or quasi drug is normally 0.001 to 99.999% by mass, preferably 0.01 to 20% by mass in terms of dried extract.

The aforementioned cosmetics contain funabarasou (*Cynanchum atratum*) or its extract as the active ingredient. The aforementioned cosmetics can contain funabarasou (*Cynanchum atratum*) or its extract alone or in combination with a carrier acceptable as cosmetics.

Examples of the carrier include an excipient, a coating agent, a binder, an expander, a disintegrant, a surfactant, a lubricant, a diluent, a dispersant, buffer, an osmotic pressure adjuster, a pH adjuster, an emulsifier, a preservative, a stabilizer, an antioxidant, a colorant, an ultraviolet ray absorber, a humectant, a thickener, an activity enhancer, an anti-inflammatory agent, a germicide, a fragrance, a flavor corrective, and an odor corrective. Also, as long as the suppressing action of funabarasou (*Cynanchum atratum*) or its extract on hair growth is not lost, the above cosmetics can contain other active ingredients and cosmetic ingredients such as a humectant, a whitening agent, an ultraviolet protectant, a cellular stimulant, a cleanser, a keratolytic agent, a make-up component (such as a cosmetic base, a foundation, a face powder, a powder, a blusher, a lipstick, an eye make-up, an eyebrow cosmetics, and a mascara).

Examples of the form of the cosmetics include any form that can be used for cosmetics such as a cream, an emulsion, a lotion, a suspension, a foam, a gel, a powder, a face pack, a sheet, a patch, a stick, and a cake. Preferably, the cosmetics can be in the form of a lotion, an emulsion, a cream, a foam, a gel, and the like for hair depilation or hair epilation.

The aforementioned cosmetics can be produced from funabarasou (*Cynanchum atratum*) or its extract, or by combining the aforementioned carriers and/or other active ingredients and cosmetic ingredients as needed, according to a routine method. The content of funabarasou (*Cynanchum atratum*) or its extract in the cosmetics is normally 0.0001 to 99.999% by mass, preferably 0.001 to 10% by mass in terms of dried extract.

The aforementioned food, drink, or feed, or its raw ingredient can be a food, a functional food, a food for the sick, a food for specified health use, a pet food, and the like containing funabarasou (*Cynanchum atratum*) or its extract as the active ingredient, or a raw ingredient of such foods. These foods are intended to exert a function such as suppression of hair growth, suppression of hair generation or hair growth, or hair depilation or hair epilation, and are labeled with such functional information as needed. The kind of the aforementioned food and drink is not particularly limited. Examples of the drink include a drink of any kind such as a fruit juice drink, a carbonated drink, a tea drink, a milk drink, an alcoholic drink, and a soft drink. The food can be in any form such as solid, semi-solid, and liquid, or it can also be in the form of a tablet, a pill, a capsule, a liquid, a syrup, a powder, a granule, and the like. Examples of the food include breads, noodles, pastas, jelly foods, various kinds of snacks, cakes, confectionery, ice creams, soups, milk products, frozen foods, instant foods, other processed foods, seasonings, and supplements. The kind of the aforementioned feed is not particularly limited either, and it may be a feed for an animal of any kind, and similarly to the case of the aforementioned foods, it can also be in an arbitrary form.

The aforementioned food, drink, or feed, or its raw ingredient can contain funabarasou (*Cynanchum atratum*) or its extract alone or in combination with other food materials and an additive such as a solvent, a softener, oil, an emulsifier, a preservative, a fragrance, a stabilizer, a colorant, an antioxidant, a humectant, and a thickener. The content of funabarasou (*Cynanchum atratum*) or its extract in the above food, drink, or feed is normally 0.0001 to 99.999% by mass, preferably 0.001 to 10% by mass in terms of dried extract.

According to yet another embodiment of the present invention, a method for suppressing hair growth, characterized by administering funabarasou (*Cynanchum atratum*) or its extract is provided. In this method, an effective dose of funabarasou (*Cynanchum atratum*) or its extract is administered for suppression of hair growth, suppression of hair generation or hair growth, or for hair depilation, hair epilation, or the like to a subject in need thereof. Alternatively, an effective dose of funabarasou (*Cynanchum atratum*) or its extract is ingested for suppression of hair growth, suppression of hair generation or hair growth, or for hair depilation, hair epilation, or the like by a subject in need thereof.

Examples of the subject of administration or ingestion include an animal, preferably a human or a non-human mammal, more preferably a human. Alternatively, the subject of administration or ingestion can be a tissue, an organ, and a cell derived from an animal, or a fraction of these materials. This tissue, organ, cell, or fraction of these materials is preferably a nature-derived or biologically or biotechnologically modified tissue, organ, cell, or a fraction of these materials capable of growing hair. Further preferably, the above tissue, organ, cell, or a fraction of these materials is derived from the skin.

Preferably, funabarasou (*Cynanchum atratum*) or its extract is applied to the area of the skin tissue of the aforementioned subject where suppression of hair growth is desired.

Preferable dose and ingestion amount can vary according to the species, body weight, sex, age, condition of the subject and other factors. The dose, route, and interval of administration and the amount and interval of ingestion can be appropriately determined by those skilled in the art. For example, when funabarasou (*Cynanchum atratum*) or its extract is applied to the human skin, the dose is preferably 0.01 to 1000 mg/day, preferably 0.1 to 100 mg/day per adult (in terms of dried extract).

EXAMPLES

Hereinbelow, the present invention will be described more specifically with reference to Examples.

Example 1

Evaluation of a Test Substance Based on the Expression of DnaJC6

(1) Procedure
(A) Preparation of an Extract of Goldthread (*Coptis japonica*)

To 40 g of the root of goldthread (*Coptis japonica*) (Shinwa Bussan Co., Ltd.), 400 mL of a 50% aqueous solution of ethanol was added, and immersion was performed at normal temperature for 13 days. The resulting solution was filtered to give an extract of goldthread (*Coptis japonica*). As a result of concentration of the extract of goldthread (*Coptis japonica*) thus obtained, it was found to have a solid content of 5.46 g. The concentration of the solid content of the extract was 1.73 wt %.

(B) Preparation of an Extract of Funabarasou (*Cynanchum atratum*)

To 40 g of the root of funabarasou (*Cynanchum atratum*) (Shinwa Bussan Co., Ltd.), 400 mL of a 50% aqueous solution of ethanol was added, and immersion was performed at normal temperature for 27 days. The resulting solution was filtered to give an extract of funabarasou (*Cynanchum atratum*). As a result of concentration of the extract of funabarasou (*Cynanchum atratum*) thus obtained, it was found to have the solid content of 4.39 g. The concentration of the solid content of the extract was 1.33 wt %.

(C) Preparation of a Culture Product

Human culture cells in which the expression of DnaJC6 is confirmed (293A, ATCC, or MeWo, Japan Health Sciences Foundation) were cultured in DMEM (Invitrogen, High glucose, 10% heat-inactivated FBS) at 37° C. under the conditions of 5% $CO_2$. The test substance was prepared at a concentration of 1 mg/ml with 50% ethanol, and then added to the medium at 0.1 vol % (a final concentration of 1 μg/ml). In the control group, an equal volume of a 50% ethanol solution (Vehicle) was added to the medium.

(D) Measurement of the Human DnaJC6 Promoter Activity

The 293A cells were transfected with the hDnaJC6opP/pGL4.10 [luc2] plasmids, in which the firefly *luciferase* gene is inserted downstream of the human DnaJC6 promoter (SEQ ID NO: 1: 979 bp [−771 to +208 relative to the transcription initiation site]), and the plasmids in which *Renilla luciferase* is introduced downstream of the CMV promoter (pRL-CMV, Promega), which were used for normalization of the transfection efficiency, using LipofectAMINE2000 reagent (Invitrogen). Eight hours later, the medium was exchanged and the test substance was added. A further 24 hours later, the luciferase activity in each group was measured.

The luciferase assay was carried out using a DUAL-GLO® Luciferase Assay System (Promega). After removal of the medium, a DUAL-GLO® luciferase reagent diluted two-fold with PBS was added, followed by stirring. Then, approximately 20 minutes later, the firefly luciferase activity was measured. Subsequently, an equal volume of DUAL-GLO®

Stop & Glo reagent was added, followed by stirring, and the *Renilla luciferase* activity was measured. The luciferase activity was measured for two seconds in both measurements.

All the DnaJC6 promoter activity (the firefly luciferase activity) was normalized by dividing it by the *Renilla luciferase* activity, which was introduced for the normalization of the transfection efficiency. Subsequently, the rate of inhibition of DnaJC6 promoter activity was obtained by the following formula and the % inhibition of DnaJC6 promoter activity by the test substance was calculated.

The rate of inhibition of DnaJC6 promoter activity(%) ={(Solvent control addition group−Test substance addition group)/Solvent control addition group}×100

(E) Real-Time RT-PCR

After adding the test substance, MeWo cells were cultured for 24 hours, and total RNA was extracted from the cells using an RNEASY® Mini Kit (QIAGEN). Total RNA was prepared in accordance with the attached instructions. After adjusting the total RNA to a uniform concentration, the total RNA was subjected to heat treatment at 65° C. for five minutes, then rapidly cooled, and then used. The reverse transcription reaction was carried out in accordance with the attached instructions with certain amounts of total RNA and Oligo(dT)$_{20}$ using a THERMOSCRIPT™ RT-PCR System (Invitrogen). The RT samples were stored at −20° C. until they were used.

Quantification of mRNA expression by Real-time RT-PCR was carried out using a POWER SYBR®-green PCR Master Mix (Applied Biosystems, Inc.) by a PCR product auto-detection/quantification system PRISM 7500 (Applied Biosystems, Inc.).

Using 50 μl of the reaction solution, real-time RT PCR was carried out under the amplification conditions including a denaturation reaction at 95° C. for 15 seconds and an annealing and extension reaction at 60° C. for one minute. The expression level of mRNA of the DnaJC6 gene was normalized based on the expression level of mRNA of RPLP0, which was the control gene. The primers used in RT-PCR were designed by using a PRIMER EXPRESS® ver. 2.0 (Applied Biosystems, Inc.). The primers used are shown in Table 1 below.

TABLE 1

| Primer | Sequence |
|---|---|
| DnaJC6 Forward | CAGGAAAGTGAGCAATCAGATGA (SEQ ID NO: 2) |
| DnaJC6 Reverse | GGCTTGTCACCATTGGCATT (NM_014787:53 bp, SEQ ID NO: 3) |
| RPLP0 Forward | TCCTGAGTGATGTGCAGCTGAT (SEQ ID NO: 4) |
| RPLP0 Reverse | AGCACTTCAGGGTTGTAGATGCT (NM_053275:151 bp, SEQ ID NO: 5) |

(F) Western Blotting

After adding the test substance, MeWo cells were cultured for 24 hours and then harvested. The cells were then solubilized using a lysis buffer (50 mM Tris-HCl, 125 mM NaCl, 0.5% NP40, pH =7.6) containing a 1% protease inhibitor cocktail (SIGMA) and then mixed with a sample buffer. The mixture was subjected to heat treatment at 100° C. for five minutes and then used for Western blotting. Polyacrylamide gel electrophoresis was performed by the standard method using a 4-20% gradient gel. The blot was transferred onto a HYBOND™ P membrane (Amersham) by a wet method. After transferring to a membrane, blocking was performed using 5% skim milk. For the primary antibody, a 1 μg/ml rabbit anti-DnaJC6 antibody, which was prepared by the standard method, was used in 5% skim milk and a 0.2 μg/ml goat anti-Actin (I-19) antibody (Santa Cruz Biotechnology, Inc.) was used in 5% skim milk. For the secondary antibody, an anti-rabbit IgG-HRP (Amersham) or an anti-goat IgG-HRP (Santa Cruz Biotechnology, Inc.) was used, and both of these antibodies were diluted to 1/2000 with 5% skim milk. The ECL development was performed using a LUMIGLO® Reagent and Peroxide (Cell Signaling Technology, Inc.) in accordance with the instructions.

(2) Results

Figure 2:
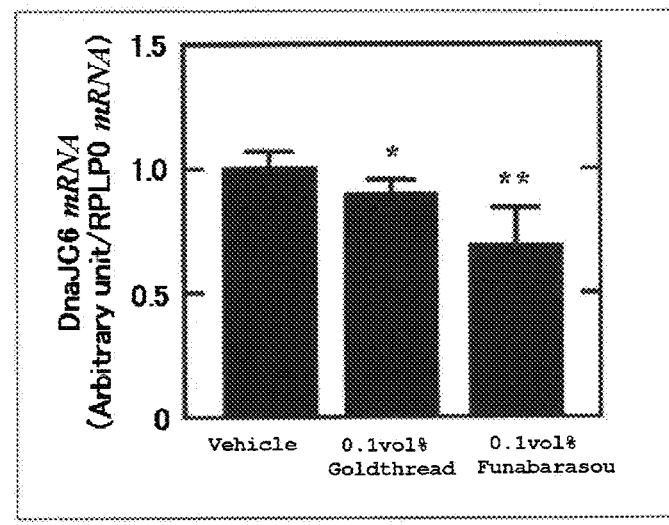
FIG. 2 shows the effect of the extract of goldthread (*Coptis japonica*) and the extract of funabarasou (*Cynanchum atratum*) on the human DnaJC6 mRNA expression. In the figure, n=3, mean±SD, *: P<0.05, **: P<0.01 (non-paired t-test, vs Vehicle).
Figure 3:
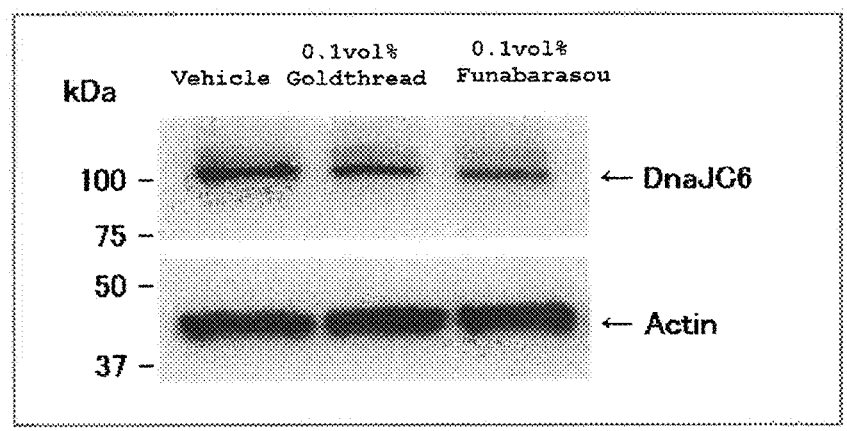
FIG. 3 shows the effect of the extract of goldthread (*Coptis japonica*) and the extract of funabarasou (*Cynanchum atratum*) on the human DnaJC6 protein expression.

The results are shown in FIGS. 1, 2 and 3. Relative to the control group (Vehicle), the DnaJC6 promoter activity and the expression of DnaJC6 mRNA were significantly suppressed, and the expression level of DnaJC6 protein was also suppressed in each of the groups administered with the extracts of goldthread (*Coptis japonica*) and funabarasou (*Cynanchum atratum*).

Example 2

Evaluation of Suppression of Hair Growth by the Test Substance Using an Isolated Human Hair Follicle A human scalp sample was sterilized by immersing it into a 0.1% chlorhexidine gluconate solution for one minute, and then washed with PBS. Subsequently, in the William E medium (Invitrogen), a hair follicle was isolated under a stereoscopic microscope with tweezers and a scalpel. The hair follicle thus isolated was cultured in the William E medium (24 well plate, 300 μl) prepared by adding 2 mM L-glutamine (Invitrogen), 10 μg/ml insulin (Invitrogen), 40 ng/ml hydrocortisone (SIGMA), and 1% Antibiotics-antimitotics (Invitrogen) under the conditions of 37° C. and 5% $CO_2$. The extracts of goldthread (*Coptis japonica*) and funabarasou (*Cynanchum atratum*) prepared in Example 1 were prepared at a concentration of 1 mg/ml with 50% ethanol and then added to the medium at 0.1 vol % (a final concentration of 1 μg/ml). As a control, an equal volume of the 50% ethanol solution (Vehicle) was added to the medium.

The organ culture of the hair was serially photographed under a microscope, and based on the scale photographed under the same conditions, the length of the hair follicle was calculated by image analysis. The image analysis was performed by a NewQube (version 4.0.3, Nexus), and the amount of increase relative to the initial value was used as the amount of extension of hair.

Figure 4:
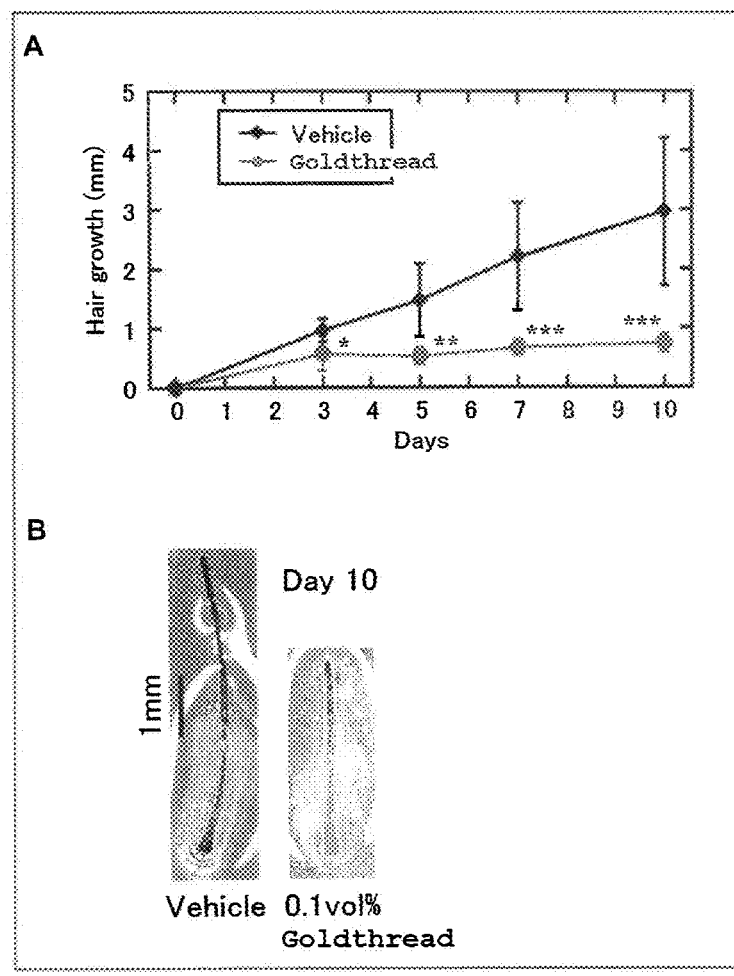
FIG. 4 shows the effect of the extract of goldthread (*Coptis japonica*) on hair growth. A: The results of chronological observation of hair growth (n=5 or 6, mean±SD, *: P<0.05, : P<0.01, *: P<0.001 (non-paired t-test, vs Vehicle). B: Images of cultured hair follicles on Day 10.
Figure 5:
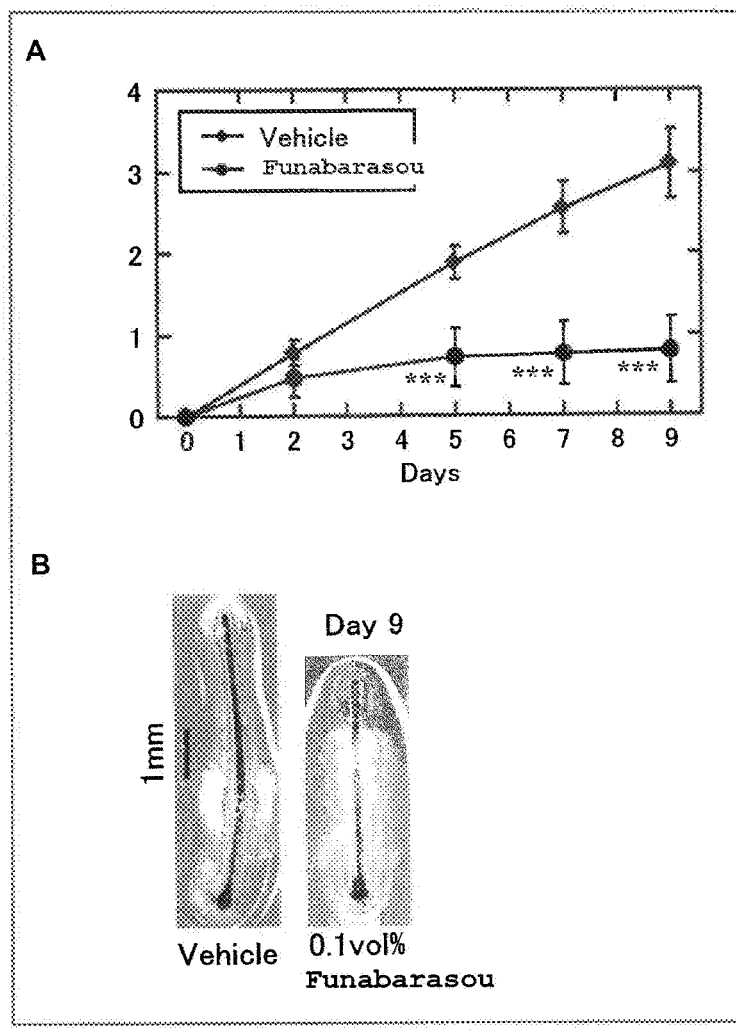
FIG. 5 shows the effect of the extract of funabarasou (*Cynanchum atratum*) on hair growth. A: The results of chronological observation of hair growth (n=10 to 14, mean±SD, ***: P<0.001 (non-paired t-test, vs Vehicle). B: Images of cultured hair follicles on Day 9.

The results are shown in FIGS. 4 and 5. In the control group (Vehicle), extension of hair follicle (hair growth) was observed in accordance with the culture time, whereas in the groups administered with goldthread (*Coptis japonica*) and funabarasou (*Cynanchum atratum*), both of which have a suppressing action on the expression of DnaJC6, the extension of hair follicle was significantly suppressed.

Production Example

Using the extracts obtained in Example 1 as the active ingredient, a lotion, a cream, an aerosol, a face pack, a foundation, a skin toner, and a gel having the compositions shown below were each prepared by a routine method.

Production Example 1

Hair Generation-Suppressing Lotion

A solution A, in which the following components A were mixed, was prepared. Separately, a solution B, in which the following components B were mixed, was prepared. The solution B was added to the solution A, and the resulting solution was uniformly mixed by stirring to give a lotion.

| | (Composition) | (Formulation: Mass %) |
|---|---|---|
| A | Polyoxyethylene hydrogenated castor oil | 0.8 |
| | Ethanol | 30.0 |
| B | Extract of funabarasou (*Cynanchum atratum*) | 1.0 (dry solid content) |
| | Sodium dodecyl sulfate | 0.12 |
| | Dodecyl methylamine oxide | 0.18 |
| | Isopropyl alcohol | 15.0 |
| | Benzyl alcohol | 15.0 |
| | Glycerin | 2.0 |
| | Purified water | Balance |

Production Example 2

Hair Generation-suppressing Cream

A solution A, in which the following components A were mixed, was prepared. Separately, a solution B, in which the following components B were mixed, was prepared. The solution B was added to the solution A, and the resulting solution was uniformly mixed by stirring, emulsified, and then cooled to give a cream.

| | (Composition) | (Formulation: Mass %) |
|---|---|---|
| A | Liquid paraffin | 10.0 |
| | Squalane | 7.0 |
| | Jojoba oil | 3.0 |
| | Solid paraffin | 3.0 |
| | Polyoxyethylene cetyl ether | 2.0 |
| | Sorbitan sesquioleate | 1.0 |
| | Potassium hydroxide | 0.1 |
| B | Extract of funabarasou (*Cynanchum atratum*) | 1.0 (dry solid content) |
| | Glycerin | 3.0 |
| | Ethylparaben | 0.1 |
| | Purified water | Balance |

Production Example 3

Aerosol

The following components A were uniformly mixed and placed in a container, which was then filled with liquefied petroleum gas B (propellant) by a routine method, whereby an aerosol was produced.

| | (Composition) | (Formulation: Mass %) |
|---|---|---|
| A | Extract of funabarasou (*Cynanchum atratum*) | 1.0 (dry solid content) |
| | Cetanol | 1.2 |
| | Propylene glycol | 4.0 |
| | Ethanol | 8.0 |
| | Purified water | Balance |
| B | Liquefied petroleum gas (propellant) | 4.0 |

Production Example 4

Hair Generation-suppressing Face Pack

The face pack having the following composition was prepared by a routine method.

| (Composition) | (Formulation: Mass %) |
|---|---|
| Extract of funabarasou (*Cynanchum atratum*) | 3.0 (dry solid content) |
| Polyvinyl alcohol | 20.0 |
| Glycerin | 5.0 |
| Ethanol | 16.0 |
| Fragrance | Trace |
| Dye | Trace |
| Purified water | Balance |

Production Example 5

Foundation

The foundation having the following composition was prepared by a routine method.

| (Composition) | (Formulation: Mass %) |
|---|---|
| Extract of funabarasou (*Cynanchum atratum*) | 1.0 (dry solid content) |
| Spherical silica beads | 20.0 |
| Silica-coated sericite | 45.0 |
| Ultrafine titanium dioxide particles | 10.0 |
| Yellow iron oxide | 3.0 |
| Talc | 5.0 |
| Mica | 5.0 |
| Red iron oxide | 1.0 |
| Ultramarine blue | 1.0 |
| Paraben | 0.2 |
| Liquid paraffin | 4.8 |
| Squalane | 4.0 |

Production Example 6

Hair Generation-suppressing Skin Toner

The skin toner having the following composition was prepared by a routine method.

| (Composition) | (Formulation: Mass %) |
|---|---|
| Extract of funabarasou (*Cynanchum atratum*) | 5.0 (dry solid content) |
| Glycerin | 15.0 |
| Dipropylene glycol | 5.0 |
| Purified water | balance |

Production Example 7

Hair Generation-suppressing Gel

The gel having the following composition was prepared by a routine method.

| (Composition) | (Formulation: Mass %) |
|---|---|
| Polyacrylic acid | 0.5 |
| Potassium hydroxide | 0.15 |
| Glucam | 10.0 |
| Glycerin | 10.0 |
| Glycine betaine | 3.0 |
| Extract of funabarasou (*Cynanchum atratum*) | 2.0 (dry solid content) |
| Succinic acid | 1.5 |
| Purified water | Balance |

The invention claimed is:

1. An in vitro method for selecting or evaluating a hair growth control agent, comprising the following steps (A) to (E):
   (A) selecting cells capable of expressing human DnaJC6;
   (B) subjecting a group of the cells to the presence of a test substance and not subjecting another group of the cells to the presence of the test substance;
   (C) measuring the expression level of DnaJC6 in both the cells that were subjected to the presence of the test substance and the cells that were not subjected to the presence of the test substance;
   (D) comparing the expression level of DnaJC6 in the cells that were subjected to the presence of the test substance and in the cells that were not subjected to the presence of the test substance; and
   (E) selecting the test substance as a hair growth control agent when there is a statistically significant difference in the expression level of DnaJC6 between the cells that were subjected to the presence of the test substance and the cells that were not subjected to the presence of the test substance, wherein a test substance that reduces the expression level of DnaJC6 is selected as a hair growth suppression agent and a test substance that increases the expression level of DnaJC6 is selected as a hair growth promoting agent.

2. The method according to claim 1, wherein the expression level of DnaJC6 is the expression level of DnaJC6 protein, the expression level of a gene or its mRNA encoding the DnaJC6 protein, or an amount of activation of a promoter of the gene encoding the DnaJC6 protein.

3. The method according to claim 2, wherein measurement of the expression level of the gene encoding the DnaJC6 protein or its mRNA is performed by polymerase chain reaction (PCR), Northern blotting, RNase protection assay, or DNA array analysis.

4. The method according to claim 2, wherein measurement of the expression level of the DnaJC6 protein is performed by Western blotting, enzyme-linked immunosorbent assay (ELISA), or radioimmunoassay (RIA) using a DnaJC6 protein-specific antibody.

5. The method according to claim 1, wherein the expression level of DnaJC6 is measured by measuring the expression level of a reporter gene the expression of which is regulated by a DnaJC6 gene promoter.

6. The method according to claim 5, wherein the reporter gene is selected from the group consisting of luciferase, chloramphenicol acetyltransferase, β-galactosidase, β-glucuronidase, and a green fluorescent protein.

7. The method according to claim 1, wherein the cell capable of expressing DnaJC6 is a cell present in a mammalian skin section, in cultured cells, or in a skin-culture product.

8. The method according to claim 1, wherein the test substance reduces the expression level of DnaJC6.

9. The method according to claim 1, wherein the test substance increases the expression level of DnaJC6.

10. An in vitro method for selecting or evaluating a hair growth control agent, comprising the following steps (A) to (E):
   (A) selecting cells capable of expressing human DnaJC6;
   (B) subjecting a group of the cells to the presence of a test substance and not subjecting another group of the cells to the presence of the test substance;
   (C) measuring the expression level of DnaJC6 in both the cells that were subjected to the presence of the test substance and the cells that were not subjected to the presence of the test substance;
   (D) comparing the expression level of DnaJC6 in the cells that were subjected to the presence of the test substance and in the cells that were not subjected to the presence of the test substance; and (E) selecting the test substance as a hair growth control agent when the expression level of DnaJC6 mRNA is increased or decreased by 10% or more in comparison to that in the cells that were not subjected to the test substance, wherein a test substance that reduces the expression level of DnaJC6 by 10% or more is selected as a hair growth suppression agent and a test substance that increases the expression level of DnaJC6 by 10% or more is selected as a hair growth promoting agent.

11. The method according to claim 10, wherein measurement of the expression level of the gene encoding the DnaJC6 protein or its mRNA is performed by polymerase chain reaction (PCR), Northern blotting, RNase protection assay, or DNA array analysis.

12. The method according to claim 10, wherein the cell capable of expressing DnaJC6 is a cell present in a mammalian skin section, in cultured cells, or in a higher order skin-culture product.

13. The method according to claim 10, wherein the test substance reduces the expression level of DnaJC6.

14. The method according to claim 10, wherein the test substance increases the expression level of DnaJC6.

15. An in vitro method for selecting or evaluating a hair growth control agent, comprising the following steps (A) to (E):
(A) selecting cells capable of expressing an expression product encoded by a reporter gene that is regulated by the human DnaJC6 gene promoter in the cells;
(B) subjecting a group of the cells to the presence of a test substance and not subjecting another group of the cells to the presence of the test substance;
(C) measuring the expression level of expression product in both the cells that were subjected to the presence of the test substance and the cells that were not subjected to the presence of the test substance;
(D) comparing the level of the expression product in the cells that were subjected to the presence of the test substance and in the cells that were not subjected to the presence of the test substance; and
(E) selecting the test substance as a hair growth control agent when the amount of the expression product of the reporter gene is increased or decreased by 20% or more in comparison to that in the cells that were not subjected to the test substance, wherein a test substance that reduces the amount of the expression product of the reporter gene by 20% or more is selected as a hair growth suppression agent and a test substance that increases the amount of the expression product of the reporter gene by 20% or more is selected as a hair growth promoting agent.

16. The method according to claim 15, wherein the reporter gene is selected from the group consisting of luciferase, chloramphenicol acetyltransferase, β-galactosidase, β-glucuronidase, and a green fluorescent protein.

17. The method according to claim 15, wherein the cell capable of expressing the reporter gene is a cell present in a mammalian skin section, in cultured cells, or in a skin-culture product.

18. The method according to claim 15, wherein the test substance reduces the amount of the expression product of the reporter gene.

19. The method according to claim 15, wherein the test substance increases the amount of the expression product of the reporter gene.

* * * * *